US005602148A

United States Patent [19]
Bobee et al.

[11] Patent Number: 5,602,148
[45] Date of Patent: Feb. 11, 1997

[54] LIQUID COMPOSITIONS BASED ON DERIVATIVES OF 1,4 SUBSTITUTED PIPERIDINE

[75] Inventors: Jean-Marc Bobee, Verrieres Le Buisson; Anne Coutel, Voegtlinshoffen, both of France

[73] Assignee: Rhone-Poulenc Rorer S.A., Antony, France

[21] Appl. No.: 391,286

[22] Filed: Feb. 21, 1995

Related U.S. Application Data

[63] Continuation of Ser. No. 104,052, filed as PCT/FR92/00215, Mar. 10, 1992, abandoned.

[30]  Foreign Application Priority Data

Mar. 13, 1991 [FR] France ................... 91 03049

[51] Int. Cl.⁶ ................................. A61K 31/445
[52] U.S. Cl. ............................ 514/326; 514/327
[58] Field of Search ..................... 514/326, 327

[56]  References Cited

U.S. PATENT DOCUMENTS

| | | | |
|---|---|---|---|
| 4,550,116 | 10/1985 | Soto et al. ................ | 514/327 |
| 4,666,905 | 5/1987 | Downs et al. ............ | 514/326 |
| 4,783,465 | 11/1988 | Sunshine et al. ........ | 514/255 |
| 4,829,064 | 5/1989 | Sunshine et al. ........ | 514/255 |
| 4,871,733 | 10/1989 | Sunshine et al. ........ | 514/212 |
| 4,975,426 | 12/1990 | Sunshine et al. ........ | 514/159 |

FOREIGN PATENT DOCUMENTS

| | | |
|---|---|---|
| 0134124 | 3/1985 | European Pat. Off. . |
| 8808302 | 11/1988 | WIPO . |
| 8809656 | 12/1988 | WIPO . |
| 8910143 | 11/1989 | WIPO . |

*Primary Examiner*—Kevin E. Weddington
*Attorney, Agent, or Firm*—Finnegan, Henderson, Farabow, Garrett & Dunner, L.L.P.

[57]  ABSTRACT

The present invention concerns aqueous pharmaceutical compositions based on 1,4-substituted derivatives of piperidine characterized in that the composition contains a solubilizing agent and does not contain a surfactant. The solubilizing agent for the active principle is polyethylene glycol.

11 Claims, No Drawings

LIQUID COMPOSITIONS BASED ON DERIVATIVES OF 1,4 SUBSTITUTED PIPERIDINE

This is a continuation of application Ser. No. 08/104,052, filed on as PCT/FR92/00215 on Mar. 10, 1992, now abandoned.

FIELD OF THE INVENTION

The present invention relates to a new pharmaceutical dosage form based on 1,4-substituted derivatives of piperidine.

BACKGROUND OF THE INVENTION

The pharmaceutical compounds which are the subject of the formulation described in the present invention are included in European Patent Application EP 134,124, which is included in the present application by reference.

These compounds, and still more specifically the following compound whose international name is ebastine or 4-diphenylmethoxy-1-[3-(4-tert-butylbenzoyl)propyl]piperidine of formula:

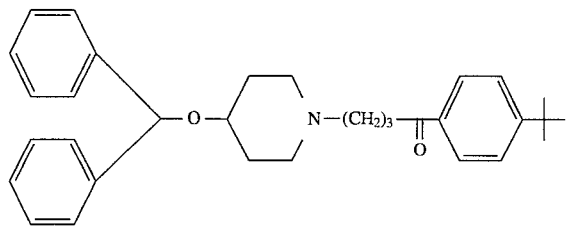

are not water-soluble. It is therefore difficult to put them into an aqueous pharmaceutical dosage form such as a syrup.

The salt formed between the above compound and lactic acid has its solubility optimum at pH 2, this solubility in any case being limited to 0.8 mg/ml, but it displays optimal stability only at pH 4. Thus, the pH values of optimal solubility and of optimal stability can in no case enable stable solutions of ebastine having a minimal concentration of 1 mg/ml to be obtained.

These compounds have antihistaminic $H_1$ activity, and are useful in the treatment of respiratory, allergic or cardiovascular disorders. Thus, they relax vascular and bronchial smooth muscle in vitro and in vivo.

They also inhibit the constricting effect of adrenaline and of potassium ions at both intestinal level and tracheal level. Thus, they block bronchoconstriction caused by histamine aerosols at doses as low as 1 mg/kg.

These compounds are active when administered parentorally and also when administered orally. When they are administered orally, it is necessary to use a salt of the carboxylic acid, the solubility of which in water is always low. Thus, in the patent application cited above, that is to say European Patent Application EP 134,124, Example 7, it was necessary, in order to form a solution, to add to the active principle described above, in its acid form, an emulsifier such as hydrogenated and ethoxylated castor oil, better known under the trade name Cremophor, at doses which are far from negligible since they are in the region of 2% by weight relative to the final solution, which represents a quantity of emulsifier equal to four times the quantity of active principle.

Now, it is always difficult in the pharmaceutical industry to offer on the market a solution which has the appearance of a soapy solution rather than that of a syrup. We hence sought to avoid the use of any emulsifier in our formulation. The emulsifier used in the composition of Patent EP 134,124 has, in addition, two major drawbacks: it has a taste which does not permit satisfactory flavoring to be obtained, and it causes intolerance phenomena resulting in vomiting of the medicament.

DESCRIPTION OF THE INVENTION

The present invention relates to a new liquid and aqueous pharmaceutical composition based on compounds corresponding to the following formula:

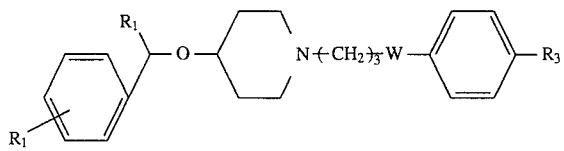

in which:

R1 represents a thienyl group, a phenyl group optionally substituted with a halogen, an alkoxy group containing 1 to 6 carbon atoms or an alkyl group containing 1 to 6 carbon atoms, R2 represents a halogen atom, a hydrogen atom, an alkoxy group containing 1 to 6 carbon atoms or an alkyl group containing 1 to 6 carbon atoms, R3 represents a halogen atom, a hydrogen atom, an alkoxy group containing 1 to 6 carbon atoms, an alkyl group containing 1 to 6 carbon atoms, an alkylthio group containing 1 to 6 carbon atoms, a cycloalkyl group containing 5 or 6 carbon atoms or a group of formula:

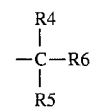

where R4 and R5 represent, independently of one another, a hydrogen atom or an alkyl group containing 1 to 6 carbon atoms and R6 represents a cycloalkyl group containing 3 to 6 carbon atoms, a hydroxymethyl or carboxyl group or alkoxycarbonyl group containing 2 to 7 carbon atoms, W represents a carbonyl or hydroxymethylene group, and their salts; characterized in that the said composition contains a solubilizing agent and does not contain a surfactant.

This composition is characterized in that the solubilizing agent for the active principle is polyethylene glycol, and preferably polyethylene glycol 600, having a molecular weight of about 600.

This composition has the advantage of not necessitating the presence of a preservative, and it is much easier to flavor than the solution containing the surfactant.

This composition contains a quantity of polyethylene glycol such that the weight ratio of the polyethylene glycol to the active principle is preferably between 100 and 500, and still more preferably between 100 and 200.

The composition of the present invention has the following advantages relative to the composition of Example 7 of the previously mentioned patent:

it no longer has either a soapy appearance or a soapy taste it no longer necessitates the presence of preservatives such as alkyl para-hydroxybenzoates it is easy to flavor it displays good preservation without any separation of particles, in contrast to what is seen in the case of the solution of Example 7.

The composition is preferably maintained at a pH of between 4 and 4.5, which is its optimum pH for stability, by adding lactic acid.

The preferred composition in syrup form according to the invention contains:

| | |
|---|---|
| ebastine | 0.1% |
| polyethylene glycol 600 | 16% |
| sweetener | 60% |
| lactic acid q.s. pH | 4.2 |
| water q.s. | 100% |

It is preferable to use Lycasin® or hydrogenated glucose syrup as a sweetener, on account of its non-cariogenic properties.

This composition is easy to flavor. It may be used in children without risk of being vomited and without incurring distaste, for the treatment allergic manifestations, most particularly of a respiratory nature.

EXAMPLES

The present invention will be described more completely by means of the examples which follow, which are not to be considered to limit the invention.

Example 1

For the preparation of this composition, the following products are employed:

| | |
|---|---|
| Ebastine | 0.100 g |
| Polyethylene glycol 600 | 16.000 g |
| Lycasin ® 80/55 (hydrogenated glucose syrup) | 60.000 g |
| N Lactic acid q.s. pH 4.2 | 0.624 g |
| Flavor | 1.000 g |
| Water q.s. | 100.000 ml |

The Ebastine, polyethylene glycol and lactic acid are mixed for 30 minutes in the heated state (between 40° and 60° C.) and with stirring. 60% of the water is added to the above mixture, the latter is stirred to homogenize and the Lycasin® is then added.

The pH is checked, and is 4.2. The complement of water is added.

This composition takes the form of a liquid which does not display any deposition after 6 months of storage.

Comparative Example According to Patent EP 134,124

The following are employed:

| | |
|---|---|
| Ebastine | 1 g |
| Lactic acid | 8.3 g |
| Glycerol | 6 g |
| Hydrogenated and ethoxylated castor oil | 4 g |
| Sodium methyl p-hydroxybenzoate | 0.32 g |

-continued

| | |
|---|---|
| Sodium propyl p-hydroxybenzoate | 0.08 g |
| Sodium saccharinate | 0.4 g |
| Flavor | |
| Sodium hydroxide q.s. | pH 4 |
| Water q.s. | 200 ml |

An aqueous solution of lactic acid and of hydrogenated and ethoxylated castor oil is added to a solution of sodium methyl and propyl p-hydroxybenzoates and of sodium saccharinate in 20 ml of water. After stirring, the Ebastine is added and the mixture is homogenized to obtain complete dissolution. After this, the flavouring agent is mixed in with vigorous stirring and the mixture is made up to the final volume with water.

The solution obtained has a very marked taste of soap and precipitates after 24 hours of storage.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A liquid pharmaceutical composition comprising:

(a) a compound corresponding to the formula:

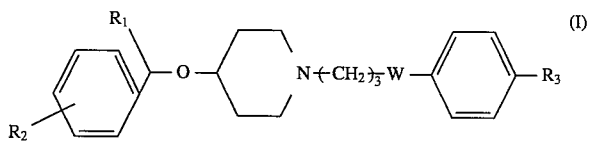

in which:

R1 represents a thienyl group; a phenyl group optionally substituted with a halogen, an alkoxy group containing 1 to 6 carbon atoms, or an alkyl group containing 1 to 6 carbon atoms, R2 represents a halogen atom, a hydrogen atom, an alkoxy group containing 1 to 6 carbon atoms, or an alkyl group containing 1 or 6 carbon atoms, R3 represents a halogen atom, a hydrogen atom, an alkoxy group containing 1 to 6 carbon atoms, an alkyl group containing 1 to 6 carbon atoms, an alkylthio group containing 1 to 6 carbon atoms, a cycloalkyl group containing 5 or 6 carbon atoms or a group of the formula:

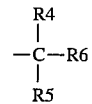

where R4 and R5 represent, independently of one another, a hydrogen atom or an alkyl group containing 1 to 6 carbon atoms, and R6 represents a cycloalkyl group containing 3 to 6 carbon atoms, a hydroxymethyl or carboxyl group or alkoxycarbonyl group containing 2 to 7 carbon atoms, and W represents a carbonyl or hydroxymethylene group or a salt of the compound of formula (I);

(b) polyethylene glycol as a solubilizing agent, said polyethylene glycol being present in a weight ratio to compound of formula I of between 100 and 500; and said composition being aqueous and having a pH between 4 and 4.5.

2. Composition according to claim 1, wherein:

R1 represents a phenyl group

R2 represents hydrogen

R3 represents a tert-butyl group

W represents a carbonyl group.

3. Composition according to claim 1, wherein the polyethylene glycol is polyethylene glycol 600.

4. Composition according to claim 1, wherein the weight ratio of polyethylene glycol to the compound of formula (I) or the salt thereof is between 100:1 and 200:1.

5. The composition of claim 1, wherein said composition contains an amount of lactic acid sufficient to maintain the pH of the composition between 4 and 4.5.

6. A method of administering a liquid pharmaceutical composition comprising the step of orally administering a pharmaceutically effective amount of the liquid pharmaceutical composition of claim 1 to a patient.

7. A syrup comprising the liquid pharmaceutical composition of claim 1.

8. A liquid pharmaceutical composition consisting essentially of:

(a) 0.1% of a compound corresponding to the formula:

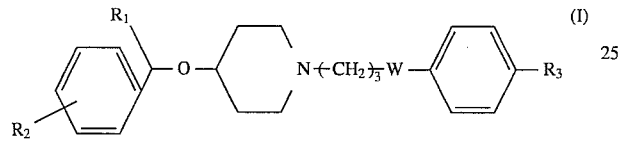

in which:

$R_1$ represents a thienyl group, a phenyl group optionally substituted with a halogen, an alkoxy group containing 1 to 6 carbon atoms or an alkyl group containing 1 to 6 carbon atoms, $R_2$ represents a halogen atom, a hydrogen atom, an alkoxy group containing 1 to 6 carbon atoms, or an alkyl group containing 1 to 6 carbon atoms, $R_3$ represents a halogen atom, a hydrogen atom, an alkoxy group containing 1 to 6 carbon atoms, an alkyl group containing 1 to 6 carbon atoms, an alkylthio group containing 1 to 6 carbon atoms, a cycloalkyl group containing 5 or 6 carbon atoms or a group of the formula:

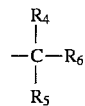

where $R_4$ and $R_5$ represent, independently of one another, a hydrogen atom or an alkyl group containing 1 to 6 carbon atoms, and $R_6$ represents a cycloalkyl group containing 3 to 6 carbon atoms, a hydroxymethyl or carboxyl group or alkoxcarbonyl group containing 2 to 7 carbon atoms, and W represents a carbonyl or hydroxymethylene group or a salt of the compound of formula (I);

(b) polyethylene glycol as a solubilizing agent; and (c) an amount of lactic acid sufficient to stabilize the composition, wherein said liquid pharmaceutical composition does not contain a surfactant.

9. The composition of claim 8 wherein the weight ratio of said polyethylene glycol to the compound of formula (I) or the salt thereof is between 100.1 and 500:1.

10. The composition of claim 8 wherein the lactic acid is present in an amount sufficient to maintain the pH of the composition between 4 and 4.5 and thereby stabilize the composition.

11. A liquid pharmaceutical composition comprising:

(a) 0.1% of a compound corresponding to the formula:

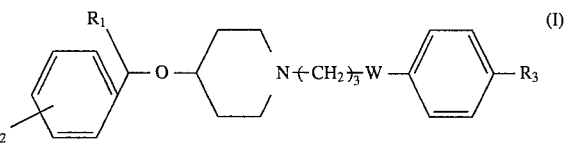

in which:

R1 represents a thienyl group, a phenyl group optionally substituted with a halogen, an alkoxy group containing 1 to 6 carbon atoms or an alkyl group containing 1 to 6 carbon atoms, R2 represents a halogen atom, a hydrogen atom, an alkoxy group containing 1 to 6 carbon atoms, an alkyl group containing 1 or 6 carbon atoms, R3 represents a halogen atom, a hydrogen atom, an alkoxy group containing 1 to 6 carbon atoms, an alkyl group containing 1 to 6 carbon atoms, an alkylthio group containing 1 to 6 carbon atoms, an cycloalkyl group containing 5 or 6 carbon atoms or a group of the formula:

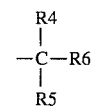

where R4 and R5 represent, independently of one another, a hydrogen atom or an alkyl group containing 1 to 6 carbon atoms, and R6 represents a cycloalkyl group containing 3 to 6 carbon atoms, a hydroxymethyl or carboxyl group or alkoxcarbonyl group containing 2 to 7 carbon atoms, W represents a carbonyl or hydroxymethylene group or a salt of the compound of formula (I);

(b) a sufficient quantity of lactic acid to adjust the pH to approximately 4.2;

(c) 16% of polyethylene glycol;

(d) 60% of sweetening agent; and (e) water in an amount to complement to 100%.

* * * * *

UNITED STATES PATENT AND TRADEMARK OFFICE
CERTIFICATE OF CORRECTION

PATENT NO. : 5,602,148
DATED : February 11, 1997
INVENTOR(S) : Jean-Marc BOBEE et al.

It is certified that error appears in the above-indentified patent and that said Letters Patent is hereby corrected as shown below:

Claim 9, column 6, line 7, "100.1" should read --100:1--.

Signed and Sealed this

Twenty-sixth Day of August, 1997

Attest:

BRUCE LEHMAN

*Attesting Officer*   *Commissioner of Patents and Trademarks*